US009281249B2

(12) United States Patent
Vaid et al.

(10) Patent No.: US 9,281,249 B2
(45) Date of Patent: Mar. 8, 2016

(54) DECOUPLING MEASUREMENT OF LAYER THICKNESSES OF A PLURALITY OF LAYERS OF A CIRCUIT STRUCTURE

(71) Applicant: GLOBALFOUNDRIES Inc., Grand Cayman (KY)

(72) Inventors: Alok Vaid, Ballston Lake, NY (US); Abner Bello, Clifton Park, NY (US); Sipeng Gu, Clifton Park, NY (US); Lokesh Subramany, Clifton Park, NY (US); Xiang Hu, Clifton Park, NY (US); Akshey Sehgal, Malta, NY (US)

(73) Assignee: GLOBALFOUNDRIES Inc., Grand Cayman (KY)

( * ) Notice: Subject to any disclaimer, the term of this patent is extended or adjusted under 35 U.S.C. 154(b) by 79 days.

(21) Appl. No.: 14/155,504

(22) Filed: Jan. 15, 2014

(65) Prior Publication Data
US 2015/0198435 A1  Jul. 16, 2015

(51) Int. Cl.
*H01L 21/66* (2006.01)
*G01B 11/02* (2006.01)
*G01B 11/06* (2006.01)
*G03F 7/20* (2006.01)
*G01N 21/21* (2006.01)

(52) U.S. Cl.
CPC ............ *H01L 22/12* (2013.01); *G01B 11/02* (2013.01); *G01B 11/065* (2013.01); *G01B 11/0633* (2013.01); *G03F 7/70616* (2013.01); *G03F 7/70625* (2013.01); *G01B 2210/56* (2013.01); *G01N 21/211* (2013.01)

(58) Field of Classification Search
None
See application file for complete search history.

(56) References Cited

U.S. PATENT DOCUMENTS 8,774,359 B1 * 7/2014 Zhuang et al. ........... 378/70
2009/0117750 A1 * 5/2009 OuYang et al. ........... 438/769

OTHER PUBLICATIONS

Bunday et al., "Gaps Analysis for CD Metrology Beyond the 22nm Node", Proc. SPIE 8681, Metrology, Inspection, and Process Control for Microlithography XXVII, 86813B (Apr. 10, 2013).*

* cited by examiner

*Primary Examiner* — Sonya D McCall Shepard
(74) *Attorney, Agent, or Firm* — Heslin Rothenberg Farley & Mesiti P.C.; Kristian Ziegler (57) ABSTRACT

Measurement of thickness of layers of a circuit structure is obtained, where the thickness of the layers is measured using an optical critical dimension (OCD) measurement technique, and the layers includes a high-k layer and an interfacial layer. Measurement of thickness of the high-k layer is separately obtained, where the thickness of the high-k layer is measured using a separate measurement technique from the OCD measurement technique. The separate measurement technique provides greater decoupling, as compared to the OCD measurement technique, of a signal for thickness of the high-k layer from a signal for thickness of the interfacial layer of the layers. Characteristics of the circuit structure, such as a thickness of the interfacial layer, are ascertained using, in part, the separately obtained thickness measurement of the high-k layer.

22 Claims, 7 Drawing Sheets

| | 3 SIGMA (CDU) IN Å | HK DOE WAFERS | | | IL DOE WAFERS | | |
|---|---|---|---|---|---|---|---|
| | | SLOT 01 | SLOT 03 | SLOT 05 | SLOT 01 | SLOT 05 | SLOT 13 |
| HK | TRADITIONAL OCD | 1.22 | 1.61 | 2.02 | 0.87 | 1.28 | 1.33 |
| | HYBRID_OCD+XPS (ADVANCED) | 0.91 | 0.87 | 1.41 | 0.77 | 1.29 | 0.94 |
| | % IMPROVEMENT | 34.1% | 85.1% | 43.3% | 13.0% | -0.8% | 41.5% |

504

| | 3 SIGMA (CDU) IN Å | HK DOE WAFERS | | | IL DOE WAFERS | | |
|---|---|---|---|---|---|---|---|
| | | SLOT 01 | SLOT 03 | SLOT 04 | SLOT 01 | SLOT 05 | SLOT 13 |
| IL | TRADITIONAL OCD | 3.13 | 3.85 | 3.71 | 3.64 | 3.47 | 3.51 |
| | HYBRID_OCD+XPS (ADVANCED) | 1.63 | 1.79 | 1.56 | 1.66 | 1.40 | 1.28 |
| | % IMPROVEMENT | 92.0% | 115.1% | 137.8% | 119.3% | 147.9% | 174.2% |

DECOUPLING MEASUREMENT OF LAYER THICKNESSES OF A PLURALITY OF LAYERS OF A CIRCUIT STRUCTURE

BACKGROUND

In the manufacture of circuit structures, quality testing is performed to determine whether circuit specifications are being met. Testing equipment has become challenged to provide the speed and precision necessary for today's applications in which the scale of these circuit structures continues to shrink, and especially when testing two/three-dimensional circuit structures. Some techniques can measure circuit structure properties concurrent with the fabrication process but may not be able to provide the necessary level of speed and precision to satisfy testing requirements for the most advanced technology.

BRIEF SUMMARY

The shortcomings of the prior art are overcome and additional advantages are provided through the provision of a method that includes: obtaining a measurement of thickness of a plurality of layers of a circuit structure, the thickness of the plurality of layers measured using an optical critical dimension (OCD) measurement technique, and the plurality of layers including a high-k layer and an interfacial layer; separately obtaining a measurement of thickness of the high-k layer, the thickness of the high-k layer measured using a separate measurement technique from the OCD measurement technique and providing greater decoupling, as compared to the OCD measurement technique, of a signal for thickness of the high-k layer from a signal for thickness of the interfacial layer; and ascertaining, by a processor, a thickness of the interfacial layer using, in part, the separately obtained thickness measurement of the high-k layer.

Additionally provided is a system including a memory; and a processor in communications with the memory, wherein the system is configured to perform a method including: obtaining a measurement of thickness of a plurality of layers of a circuit structure, the thickness of the plurality of layers measured using an optical critical dimension (OCD) measurement technique, and the plurality of layers including a high-k layer and an interfacial layer; separately obtaining a measurement of thickness of the high-k layer, the thickness of the high-k layer measured using a separate measurement technique from the OCD measurement technique and providing greater decoupling, as compared to the OCD measurement technique, of a signal for thickness of the high-k layer from a signal for thickness of the interfacial layer; and ascertaining a thickness of the interfacial layer using, in part, the separately obtained thickness measurement of the high-k layer.

Further, a computer program product is provided including a computer readable storage medium readable by a processor and storing instructions for execution by the processor to perform a method including: obtaining a measurement of thickness of a plurality of layers of a circuit structure, the thickness of the plurality of layers measured using an optical critical dimension (OCD) measurement technique, and the plurality of layers including a high-k layer and an interfacial layer; separately obtaining a measurement of thickness of the high-k layer, the thickness of the high-k layer measured using a separate measurement technique from the OCD measurement technique and providing greater decoupling, as compared to the OCD measurement technique, of a signal for thickness of the high-k layer from a signal for thickness of the interfacial layer; and ascertaining a thickness of the interfacial layer using, in part, the separately obtained thickness measurement of the high-k layer.

Additional features and advantages are realized through the concepts of the present invention. Other embodiments and aspects of the invention are described in detail herein and are considered a part of the claimed invention.

BRIEF DESCRIPTION OF THE DRAWINGS

Aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION

Due to circuit structure integration schemes for circuits approaching, at, or exceeding the 14 nm node, the measurement or determination of circuit structure characteristics is performed directly on the circuit structure during fabrication thereof. Some circuit structures, such as fin field-effect transistor (FinFET) circuit structures, are inherently complex owing to their two/three-dimensional construction in combination with potentially several underlying layers. Some properties of relatively complex circuit structures like a FinFET, such as thickness of layer(s) of material formed at/on the outer surfaces of these structures, are not as easily measurable as comparatively flat structures on a flat pad surface or flat silicon surface, for instance.

Several workhorse planar metrology techniques, such as ellipsometry or x-ray reflectance, may be inadequate especially when measuring properties of three-dimensional structures because those technologies are unable to adequately account for the effect that the shape of the structure has on the measurements of material thickness being detected. Even techniques that can traditionally accommodate more complex 2D/3D structures, such as Optical Critical Dimension (OCD), scatterometry, x-ray spectroscopy, or x-ray photoelectron spectroscopy (XPS) techniques, can have difficulty accurately measuring some ultra-thin layers or complex profiles (rounding, spacer pull-down, etc.). For instance, some techniques can't differentiate the locations from which particular signals (such as signals indicative of the presence of Silicon) are coming. Further, OCD is a technique typically used in measuring layer thickness of interfacial and a "high-k" dielectric layers, which are formed at the top of FinFET structures during fabrication thereof. Realistic specifications for layer thickness for a FinFET structure may be 16 A for the high-k layer and 9 A for the interfacial layer (IL), with an acceptable deviation up to 1% of nominal (0.16 A or 0.09 A, respectively). This presents challenges for OCD when measuring such thin layers disposed on top of protruding circuit structures.

Nonetheless, the thicknesses of these layers can be critical to the electrical performance of the device and proper measurement is therefore vital for QC purposes. Additionally, it may be necessary to monitor these properties inline, e.g. non-destructive measurement as part of the production line, due to the tight specifications of the circuit and their impact on electrical performance (equivalent oxide thickness, threshold voltage, etc.). In the case of interfacial and high-k thickness, it may be necessary to measure these layers simultaneously and rapidly due to the limited amount of time ("queue time") between layer formation, for instance the time between the deposition of the high-k layer and overlying layer(s) (such as Titanium-Nitride layer). Sometimes the queue time between formation of successive layers is too short to allow measurement, as may be the case with formation of the interfacial and high-k layers (see below). The queue time may be very short because electrical properties of the circuit structure can degrade quickly between process steps.

Drawbacks of existing technology that simultaneously measures properties of a circuit structure having multiple materials includes difficulty in decoupling a signal obtained to separate the contribution of one material to the signal from the contribution of other material(s) to the signal. Aspects described herein can address this. Examples are described herein within the context of measuring layer thickness of a circuit structure, e.g. FinFET, though this technique can be applied in the measurement of other characteristics and other types of circuit structures.

Figure 1:
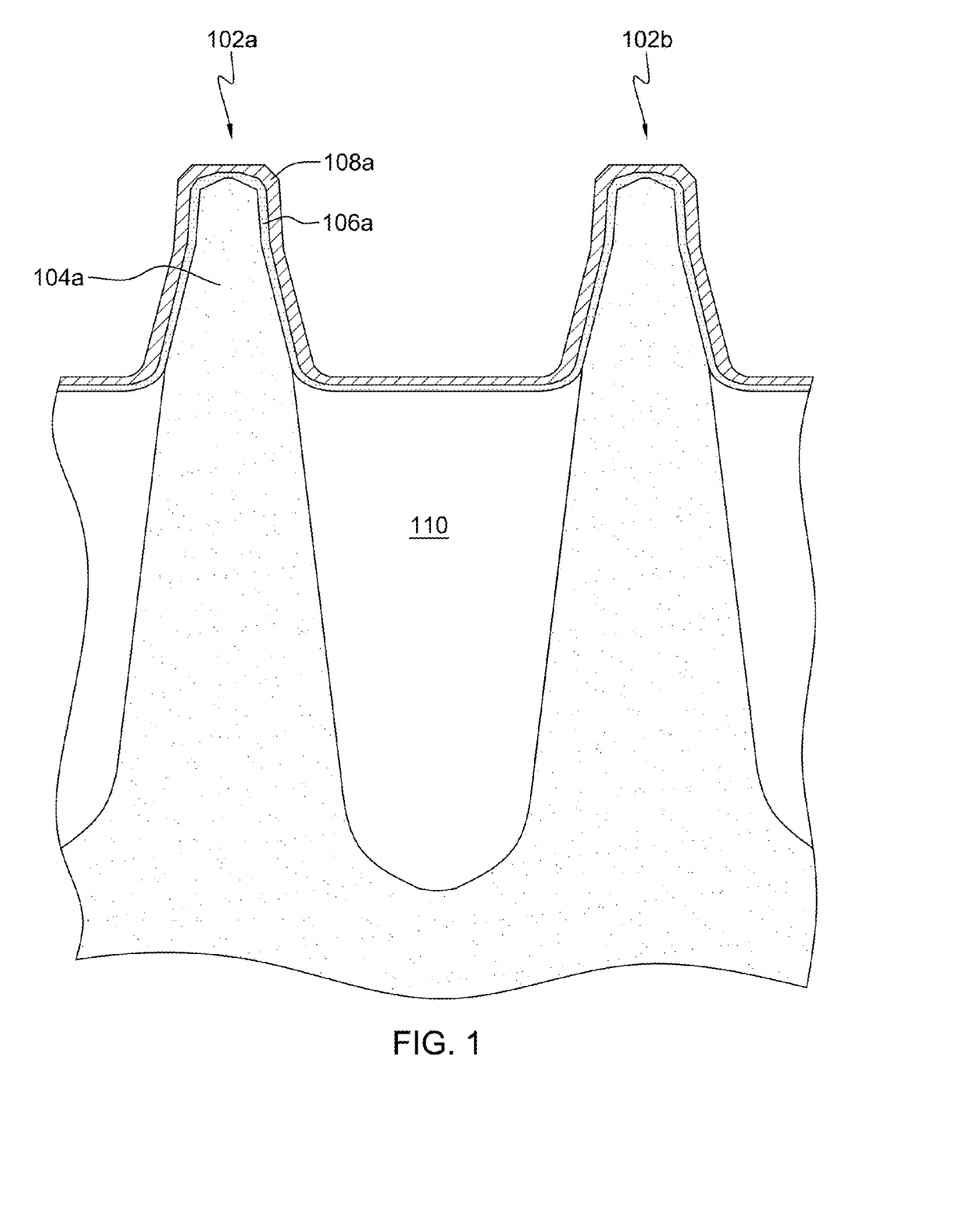
FIG. 1 depicts example circuit structures for which characteristics may be ascertained in accordance with aspects described herein.

FIG. 1 depicts example circuit structures for which characteristics may be ascertained in accordance with aspects described herein. The ascertaining may include decoupling measurement of layer thicknesses. In FIG. 1, two identical FinFET circuit structures 102a, 102b are depicted and the testing objective includes measuring the thickness of two thin films (interfacial layer and high-k material) formed at the top of each FinFET. FinFET 102a includes a fin portion 104a made of silicon. FinFET 102a is capped with a thin oxide layer (interfacial layer 106a) of, in this example, silicon oxide ($SiO_2$) formed directly over fin portion 104a. A high-k material (such as hafnium oxide, $HfO_2$) 108a is deposited over interfacial layer 106a. FinFET 102b is identical in composition and structure to FinFET 102a. Shallow trench isolation (STI) silicon oxide 110 is deposited in the trenches between the FinFETs.

The presence of interfacial layer 106a may be due to the practical impossibility of avoiding oxidation of pure silicon during the fabrication process. The silicon fin material is pure silicon immediately after it is cleaned, but it may instantly begin to oxidize, even in a good vacuum. It may be necessary therefore to control the properties of that oxide to make it as thin as possible. Part of that control includes quickly depositing the high-k material. The silicon oxide layer would ideally be infinitely thin or nonexistent, but an acceptable target thickness for present applications is about 9 A. The high-k material is deposited over the interfacial layer and serves, in this example, as the gate material in the FinFET.

Aspects described herein may be used to ascertain characteristics of not only FinFETs but other types of circuit structures/stacks. These include gate between fins, gate over fin, fins inside gate, fins between gates, and any other structures formed using any variety of techniques (such as epitaxial growth (EPI)).

Figure 2:
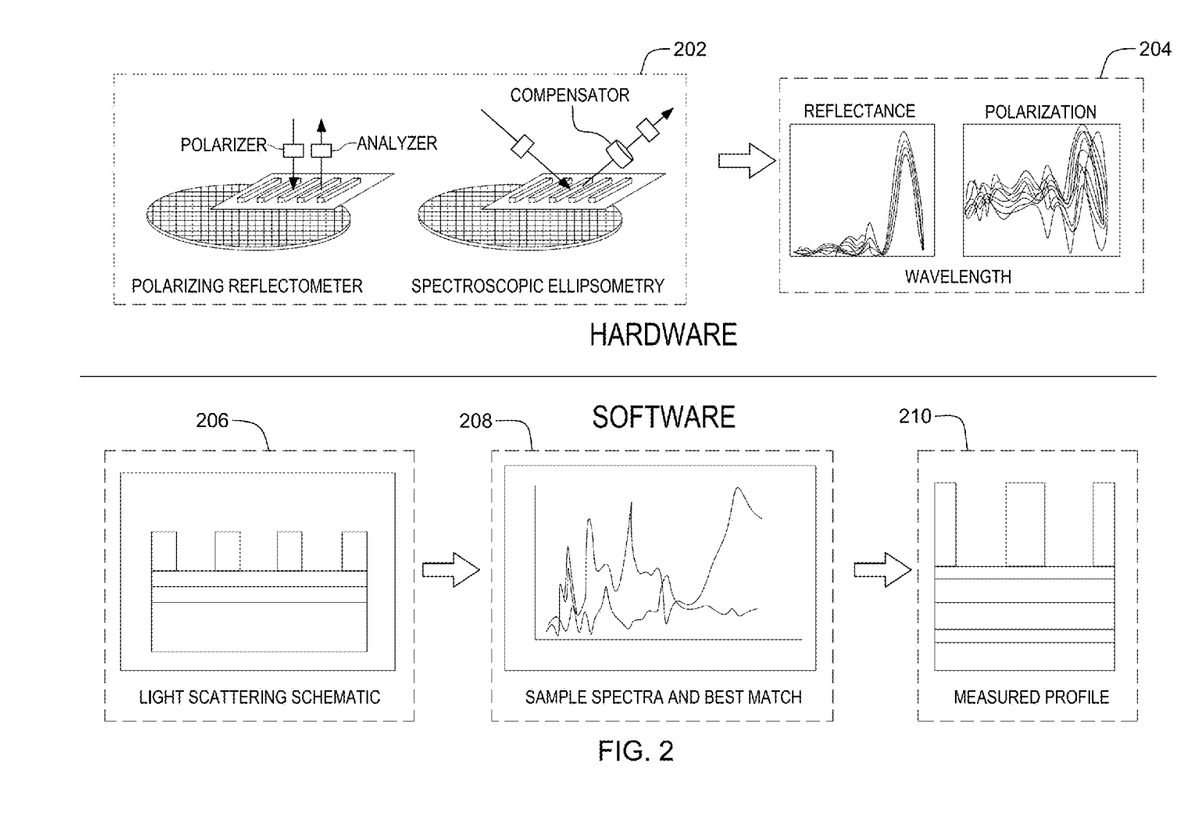
FIG. 2 depicts an overview of an Optical Critical Dimension measurement technique for use in connection with aspects described herein.

Current techniques for simultaneously measuring thickness of the interfacial and high-k layers of a FinFET of FIG. 1 may involve a scatterometry or optical critical dimension (OCD) measurement technique. Aspects described herein may build on such techniques to provide more accurate measurement. FIG. 2 depicts an overview of an Optical Critical Dimension measurement technique for use in connection with aspects described herein.

FIG. 2 presents the major process steps in OCD measurement. Incident light strikes the circuit structure(s) and the reflected light is detected using one or more of various techniques that may include polarizing reflectometry or spectroscopic ellipsometry, as examples (202). The incident light may be of normal or angled incidence with respect to the sample, and may or may not be polarized. The reflected light may pass through a compensator on its way to a detector. The output (204) of the detector, a scatterometer, or another data processing system, is in the form of two graphs (in this example). One graph is an indication of the intensity of the different reflected wavelengths (Reflectance) and the other graph is an indication of how polarization changed (Polarization). These spectra can then be used as inputs to model characteristics, like dimensions and shape, of the circuit structure(s). Complex software algorithms may be executed to analyze the spectra and produce a "ray tracing" (light scattering schematic, 206) representing how the incident light interacted with the material of the circuit structure(s). The ray tracing is then matched or 'fit' to some spectra of a known structure profile, and that structure profile is selected to represent the actual circuit structure profile.

There are different schemes for performing this fit. One such scheme is to use a library of reference spectra corresponding to different structures. The library may be built by irradiating actual structures, detecting the outputs, and storing them as spectra in the library. This may be performed numerous times through variations of different lighting characteristics (angle of incidence, intensity, etc). The result is a library of possibly thousands of distinct spectra.

In the OCD model, rather than calculating a fitting or a sample spectral in real-time, the modeled spectra in the library can be accessed and compared to the sample spectra to identify a best match (208 of FIG. 2). The measured profile can then be modeled (210) as the structure from which the best match spectra in the library was produced.

The OCD technique may work fairly well when characterizing properties of simpler stacks but may be inadequate at characterizing some properties of more complex stacks, such as three-dimensional circuit structures having thin films. The OCD measurements strongly consider the geometry of the structure. With respect to high-k and interfacial layer thicknesses, because there is little optical difference between hafnium oxide (high-k material) and silicon oxide (interfacial material), which is the basis of the OCD measurement, there is strong coupling between the layers and therefore the thickness measurement. In other words, the OCD is unable to decouple and tell the difference between the high-k and interfacial layer if either changes in thickness. For instance, an increase in the thickness of the high-k material of a FinFET is sometimes instead seen in the OCD model as an increase in thickness of the interfacial layer, and vice versa.

According to aspects described herein, a new methodology is provided for effectively decoupling measurement of the properties of one feature of a circuit structure from those of another feature of the circuit structure. Using the examples above, the measurement of the thickness of the high-k layer of a FinFET is decoupled from the measurement of the thickness of the interfacial layer of the FinFET. In this example, the high-k layer thickness is measured using a different toolset, separate from the OCD technique, that is able to effectively and accurately measure the high-k thickness on the complex circuit structure. Electron based techniques such as electron probe microanalysis can provide such ability. Example approaches include x-ray photon spectroscopy (XPS) and x-ray fluorescence (XRF). Using XPS as an example, it is able to effectively measure the high-k thickness within specification, as XPS can be shown to have accuracy to approximately 0.06 A for high-k material.

Figure 3:
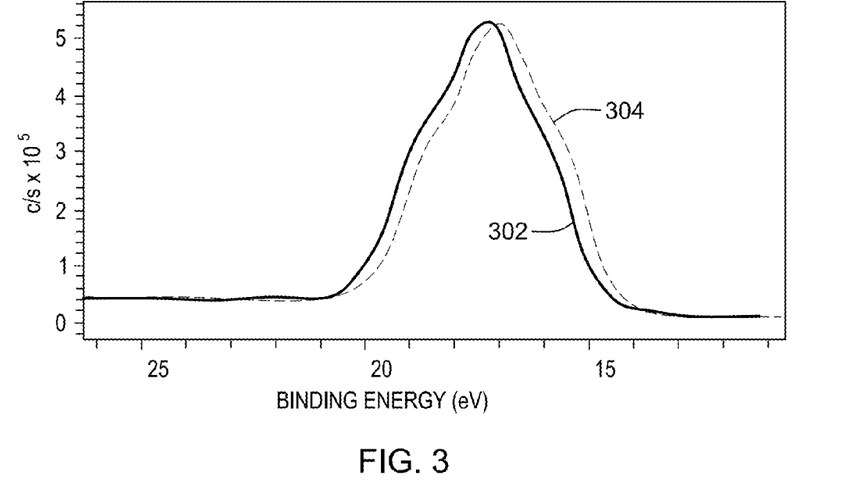
FIG. 3 depicts one example of an emitted signal produced using a measurement technique separate from an Optical Critical Dimension measurement technique, and indicative of thickness of a layer of a circuit structure, in accordance with aspects described herein.

The measurement by way of the separate technique (XPS, XRF, etc) can decouple the high-k layer signals from the interfacial layer signals to provide a measurement of the thickness (in this example) of the high-k material. Measurements using these techniques are element-specific, where the signal from the high-k comes from only the high-k material, which in this case is hafnium oxide. Thus, the measurement of this separate measurement technique looks at photoelectrons from the hafnium. FIG. 3 depicts one example of an emitted signal produced using a measurement technique separate from an Optical Critical Dimension measurement technique, and indicative of thickness of a layer of a circuit structure, in accordance with aspects described herein. In the graph of FIG. 3, an XPS spectrum (302) for hafnium is plotted against an electron binding energy (304) for pure hafnium. A shift in the spectrum indicates a different chemical state of the element, but here the correlation is clearly very high. Here, the hafnium spectrum 302 is detected from hafnium binded to oxygen to form the hafnium-oxide layer.

In FIG. 3, the spectrum from just the hafnium atoms is decoupled and independent from signals of the other elements that may be present (oxygen, silicon, nitrogen). Being element specific, however, XPS cannot measure, e.g., interfacial layer thickness because it cannot decouple the interfacial layer ($SiO_2$) signal from the underlying STI oxide which is also $SiO_2$ (in this example). The interfacial layer is made out of silicon oxide, and because there is an abundance of silicon oxide surrounding the circuit structure, the photoelectrons from silicon and oxygen of the surrounding material would pollute the singles for the silicon and oxygen from the interfacial layer. The STI material between the fins, for instance, is silicon oxide, which looks identical, from an XPS standpoint, to the interfacial layer silicon oxide on top of the fin. The oxygen and silicon readings would be a composite of the signal from the interfacial layer along with the signal from the STI silicon oxide.

Figure 4:
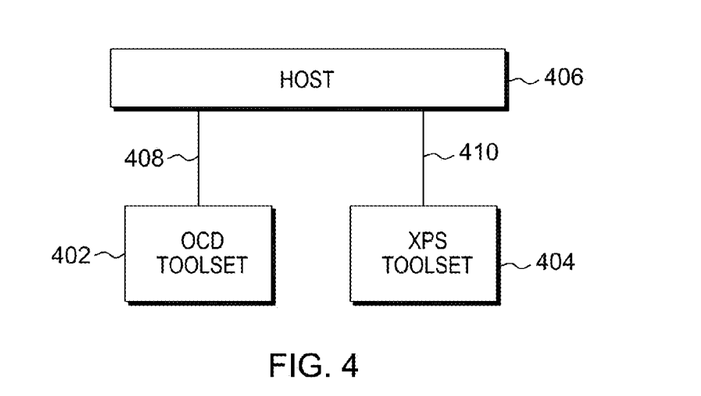
FIG. 4 depicts one example of a host system in communication with multiple separate measurement toolsets, in accordance with aspects described herein.

The separate measurement technique may include a toolset to be used in conjunction with another toolset, such as the OCD model. The separate toolset can provide information that the other toolset can use in characterizing properties of the circuit structure. This process can be facilitated using a host, which in one example is a data processing system. FIG. 4 depicts one example of a host system in communication with multiple separate measurement toolsets, in accordance with aspects described herein.

Referring to FIG. 4, an OCD toolset 402 is in communication with host 406 across a communication path 408, and a separate (XPS in this example) toolset 404 is in communication with host 406 across communication path 410. A toolset refers to a measuring tool associated with the fabrication equipment. It includes some or all of the hardware equipment and software for implementing the technique (OCD, XPS, etc) of the particular toolset. The toolset has an associated data processing system that can communicatively connect to networked host data processing system(s) across a communication path. A communication path can include hardware and software providing one or more wired or wireless connections for sending, receiving, or relaying data. In one example, a communication path includes network connections across one or more networks.

Part of the communication between a host and a given toolset identifies for the host which particular component (such as a wafer or die) is being measured by that toolset at a given time. Not every individual component produced is tested in the QC process. Typically only a subset of the lot produced is tested so that the components can move faster through the fabrication facility. Consequently, each toolset should identify to the host the particular components being tested, along with test results of that testing.

According to aspects described herein, the XPS toolset 404 feeds test data, for instance the high-k thickness measurement data, to host 406 and host 406 can provide the data to the OCD model toolset 402. The high-k thickness measurement data need not necessarily be an actual thickness value for the layer of high-k material. It may be, for instance, data describing the detected signal associated with the high-k material. In one example, the data is a spectrum of the detected signal and the OCD toolset may further process that spectrum to determine a high-k thickness value as measured by the separate technique. In other examples, the XPS toolset may further process the signal and provide the result to the host for relaying to the OCD toolset.

In some examples, the OCD toolset pulls this data, but in other examples, the host pushes the data to the OCD toolset. The OCD toolset can then use the separately obtained thickness measurement data of the high-k layer in the OCD model's determination of interfacial layer and/or high-k layer thickness. In this manner, the XPS data (in this example) is received for use by the OCD model. In one example, the data is provided as a recipe variable from a database of the host (again, created using XPS data in this example) to the appropriate equipment (OCD in this example) within a Process Job creation message.

A hybrid, or advanced, OCD model can use the high-k thickness data from the separate measurement technique to facilitate decoupling measurement of the high-k and interfacial layer thicknesses as measured by the OCD technique, to generate more accurate interfacial layer thickness results. The OCD advanced model may also be able to determine other circuit structure properties using that data, including fin critical dimension (width), height, or sidewall angle, among others.

The thickness measurement of the high-k material is just one variable in a complex determination made by the OCD model of a fit being performed between measurement(s) of the OCD process and a library of known profiles. The manner in which the data from the separate measurement technique is used may vary. In one example, the thickness measurement produced from the separate measurement technique can be fixed in the OCD model so that when the "fit" is performed, the high-k value derived from the separate measurement technique remains as that fixed value. In this case, the high-k thickness variable in the global fit remains fixed (effectively eliminating it as a variable).

In other examples, the high-k measurement provided by the separate technique is fine-tuned by the OCD model to produce even greater accuracy for the high-k thickness value. Accordingly, the thickness measurement produced from the separate measurement technique may be used as a seed value for the global fit, in which the high-k variable in the global fit is seeded to be the high-k measurement from the separate technique and weighted such that this variable value changes very minimally relative to the other variables (such as the interfacial layer thickness) in the fit. This approach tempers the amount acceptable deviation in the high-k value in the OCD model.

Figure 5:
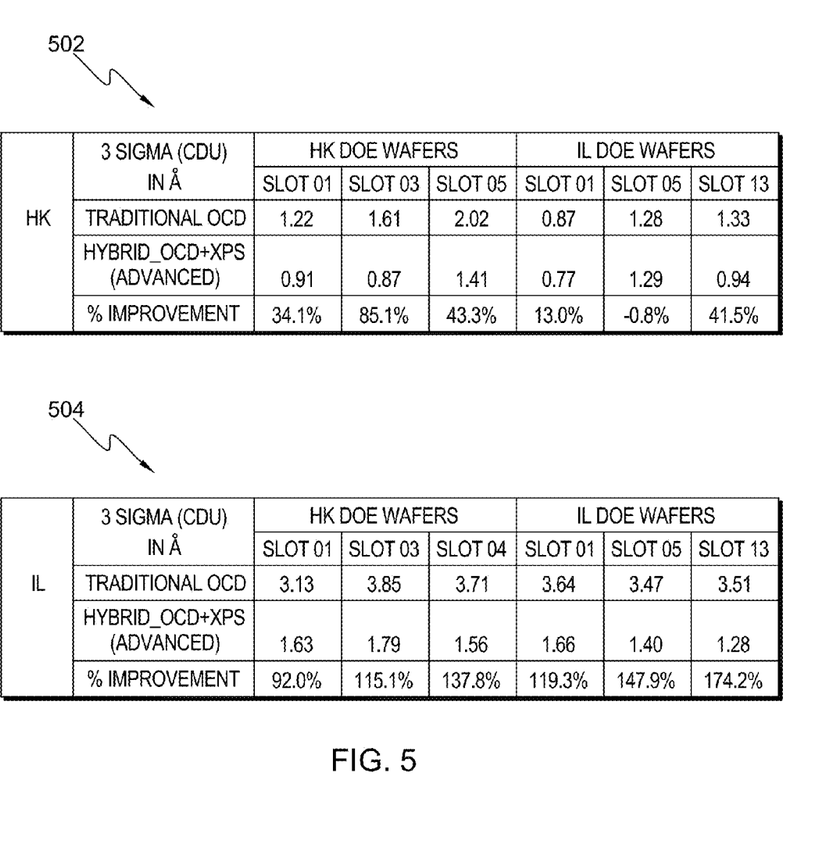
FIG. 5 presents layer thickness measurement data of a traditional OCD process as compared to a hybrid Optical Critical Dimension/XPS process that decouples measurement of layer thicknesses, in accordance with aspects described herein.

The OCD model is therefore able to decouple the composite high-k and interfacial layer measurement into individual high-k and interfacial layer thicknesses. Based on the decoupling of at least some of the OCD measurement data, improvements are made in the accuracy of the determined circuit structure properties. FIG. 5 presents layer thickness measurement data of a traditional OCD process as compared to a hybrid Optical Critical Dimension process decoupling layer thickness measurement, in accordance with aspects described herein. The tables presented in FIG. 5 highlight the improvement in layer thickness measurement accuracy based on this decoupling.

Table 502 shows improvement in high-k layer thickness determination between a traditional OCD process as compared to a hybrid OCD and separate measurement (XPS in this example) process. Two, 3-σ Design of Experiments (DOE) were performed varying a circuit structure property across multiple samples ('slots' in FIG. 5). Each sample in this example is a wafer housed in a slot of a standard container. The units of the values for Traditional OCD and Hybrid_OCD+XPS are standard deviations in angstroms. The closer the value is to 0, the better. In one 3-σ DOE, high-k thickness was varied across three slots. The hybrid technique that decoupled the combined high-k and interfacial layer measurement of the OCD model improved accuracy for the three high-k thicknesses measurements by 34.1%, 85.1% and 43.3%. In another DOE of Table 502, interfacial layer thickness was varied across three slots. The statistically significant results show that the hybrid technique that decoupled the combined high-k and interfacial layer measurement of the OCD model improved accuracy by, e.g. 13.0% and 41.5%.

Table 504 shows the improvement in interfacial layer thickness determination between a traditional OCD process versus a hybrid OCD and separate measurement (XPS in this example) process. As before, two, 3-σ DOEs were performed varying a circuit structure property across three slots. In the first DOE, high-k thickness was varied across three slots and the accuracy of all three slots in the measured interfacial layer thickness was improved by 92.0%, 115.1% and 137.8%. In the second DOE of Table 504, interfacial layer thickness was varied across three slots and the accuracy in the measured interfacial layer thickness was improved by 119.3%, 147.9% and 174.2%.

It is seen that in many cases, the accuracy is improved from 3-4 Å to 1-2 Å. Such improvement in accuracy is significant when dealing with transistors and other circuit structures at the 20 nm and 14 nm nodes. Significantly better metrology performance is derived, including: better 3-sigma critical dimension uniformity (CDU) across the wafer; better precision (short-term dynamic repeatability—STDR—15X); better matching to reference; and better DOE tracking. The methodology described herein can be used in various metrology applications such as FinFET and other complex 2D/3D circuit structures.

In the example described above, the OCD toolset (i.e. a data processing system thereof) obtains the separately obtained thickness measurement for the high-k material and ascertains thickness of the interfacial layer, high-k layer, and possibly other properties of the circuit structure. It may then output the results to the host for further handling, such as presentation to manufacturing execution systems (MES), Enterprise Resource Planning (ERP), and/or Supervisory Control and Data Acquisition (SCADA) software of the fabrication facility.

Alternatively, the ascertaining of one or more of these properties may be performed instead by one or more other data processing systems, such as a data processing system of the host system (FIG. 4, #406), of an MES, ERP, or SCADA system, or one or more other data processing systems in communication with the OCD toolset. The appropriate data of the OCD toolset and the appropriate data of the separate toolset can be provided to the other data processing system(s) which then executes instructions to ascertain, based on the obtained data, circuit structure characteristics, such as interfacial and high-k layer thicknesses, among other properties.

In some embodiments, the ascertaining of circuit structure properties is performed in-line—that is, during fabrication of the circuit structure. The OCD measurement technique and separate measurement technique may be performed at various points in the fabrication process. They may be performed at the same or different points. In particular embodiments, the process is performed directly after the high-k layer is formed at the top of the circuit structure. Aspects described herein for performing this ascertaining may be integrated into or implemented alongside current processes and hardware involved in the fabrication of the circuit structures. If implemented in-line, a wafer being tested may spend 10-15 minutes in the XPS toolset, then move to the OCD toolset for approximately 5 minutes while the advanced OCD model ascertains circuit structure properties using, for instance, the separate measurement data from the XPS toolset. Results may then be immediately and automatically provided to the host or another data processing system and displayed for a user.

Additionally or alternatively, the ascertaining may be performed offline (rather than during the fabrication of the circuit structure) as a post-build quality control or analysis. Such offline activity may be performed by various simulation software conventionally used to predict measurement performance. The simulation software conventionally produces only a 'ballpark' determination, at best, of measurement performance, for instance using noise models for various equipment along with known formulae/phenomenon from literature during the prediction. Measurement performance Delta between actual in-line results and simulation/prediction software results may be a function of complexity of structure and errors associated with assumptions made in the standard simulation software. Simulation software is just one example of a facility that can perform the ascertaining as post-build QC and/or analysis; others are possible.

Figure 6:
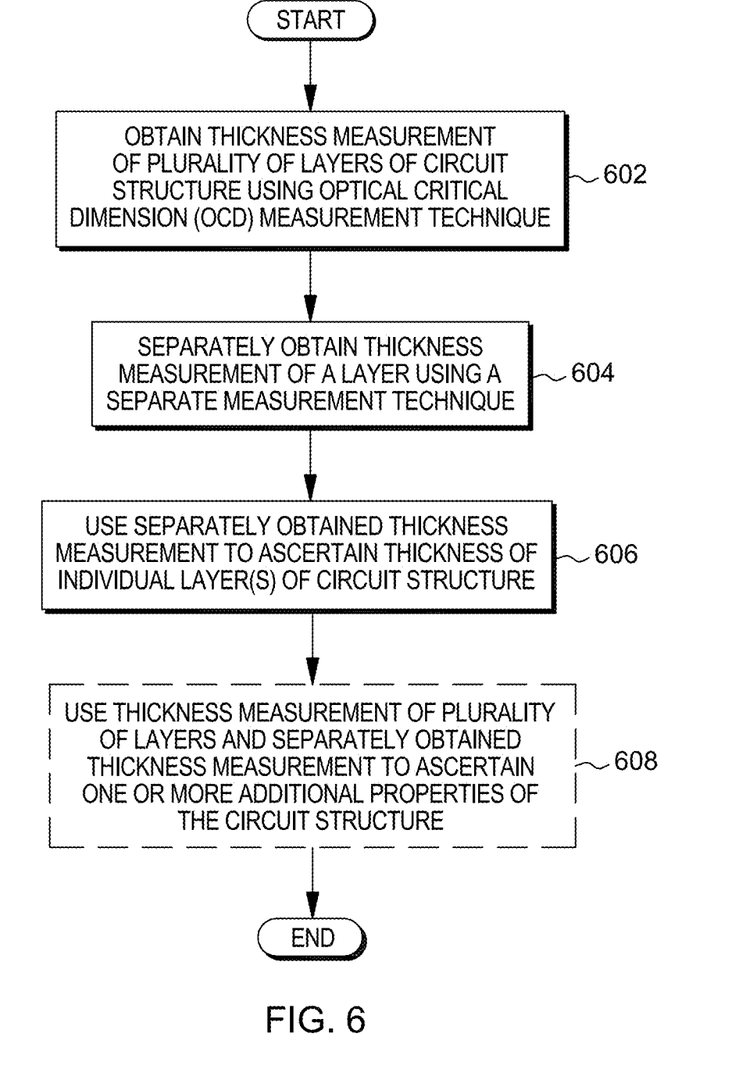
FIG. 6 depicts one example of a process for ascertaining characteristics of a circuit structure, in accordance with aspects described herein.

According to aspects described herein, processes are provided for ascertaining characteristics of a circuit structure, which involves determining individual values for elements that may otherwise be coupled together are part of a measurement of a toolset. The circuit structure is in some examples a three-dimensional structure having surface(s) that protrude from another surface or STI material. In particular embodiments, the characteristics include thicknesses of layers disposed at, or over the top of, the protruding surface(s) of the three-dimensional circuit structure. Examples of a three-dimensional circuit structure include a FinFET or a nanostructure. FIG. 6 depicts an example of such a process wherein the characteristics are layer thicknesses. In some cases, one or more aspects of the process of FIG. 6 (such as the particular measurements being performed, or the entirety of FIG. 6) are performed concurrently during fabrication of the circuit structure.

The process includes obtaining a measurement of thickness of a plurality of layers of a circuit structure, measured using an Optical Critical Dimension (OCD) measurement technique (602). The thickness measurement obtained may be in the form data produced by the OCD measurement technique. The OCD measurement technique may include measuring a coupled, or composite, thickness of multiple layers of the plurality of layers, for instance a combined thickness of two consecutive layers. The plurality of layers may include an interfacial layer and a high-k dielectric layer, and the measurement of the composite thickness may be a measurement that includes thickness of the interfacial layer and thickness of the high-k layer. The actual thicknesses of these two layers are coupled in the measurement since the measurement indicates a combined thickness for both layers. That is, the thickness of the high-k layer is coupled to the thickness of the interfacial layer as measured in the OCD measurement technique.

The process of FIG. 6 also includes separately obtaining another measurement i.e. that of thickness of a layer of the plurality of layers, measured using a separate measurement technique (604). The separate measurement technique is separate from the OCD measurement technique, and the another thickness measurement obtained may be in the form data produced by the separate measurement technique. The separate measurement technique may include detecting an emitted signal unique to one of the layers of the circuit structure, and may produce a corresponding spectra unique to that layer. Using the example above, the thickness of the high-k layer may be measured using the separate measurement technique, which may detect signal(s) for thickness of the high-k layer as distinct from signal(s) for thickness of the interfacial layer and thus can provide greater decoupling, as compared to the OCD measurement technique, of signal(s) being detected. The separate technique may provide greater decoupling because it produces a signal unique to a particular feature, such as thickness of a particular layer. The separate measurement technique includes, in some embodiments, an electron-based measurement technique, such as x-ray photoelectron spectroscopy, x-ray fluorescence spectroscopy, or electron probe microanalysis.

Next, the separately obtained thickness measurement is used to ascertain thickness of individual layer(s) of the circuit structure (606). Ascertaining the thickness of the interfacial layer includes using both the thickness measurement of the plurality of layers (from the OCD measurement technique) and using the separately obtained thickness measurement of the high-k layer. These two items (among others) may be used in an OCD model of the OCD measurement technique to ascertain the thickness of the interfacial layer. Usage in this context can including using the separately obtained thickness measurement of the high-k layer as a seed value in the OCD model to facilitate decoupling, in the OCD model, the thickness of the high-k layer from the thickness of the interfacial layer as measured in the OCD measurement technique. The seed value may be used to fix a variable for the thickness of the high-k layer in the OCD model. Alternatively, the seed value may be used for weighing a variable for the thickness of the high-k layer in the OCD model. For instance the variable may be seeded to the seed value and then weighted so that its fluctuation in a fitting process to fit the OCD measurement(s) to a predefined model is much less than it would otherwise be if unweighted.

Optionally, the thickness measurement of the plurality of layers and the separately obtained thickness measurement can be used to ascertain one or more additional properties of the circuit structure (608). For instance, the thickness measurement of the plurality of layers and the separately obtained thickness measurement of the high-k layer in the OCD model may be used to ascertain critical dimension, height, and/or sidewall angle of the circuit structure, among other characteristics thereof.

Those having ordinary skill in the art will recognize that aspects of the present invention may be embodied in one or more systems, one or more methods and/or one or more computer program products. In some embodiments, aspects of the present invention may be embodied entirely in hardware, entirely in software (for instance in firmware, resident software, micro-code, etc.), or in a combination of software and hardware aspects that may all generally be referred to herein as a "system" and include circuit(s) and/or module(s).

Figure 7:
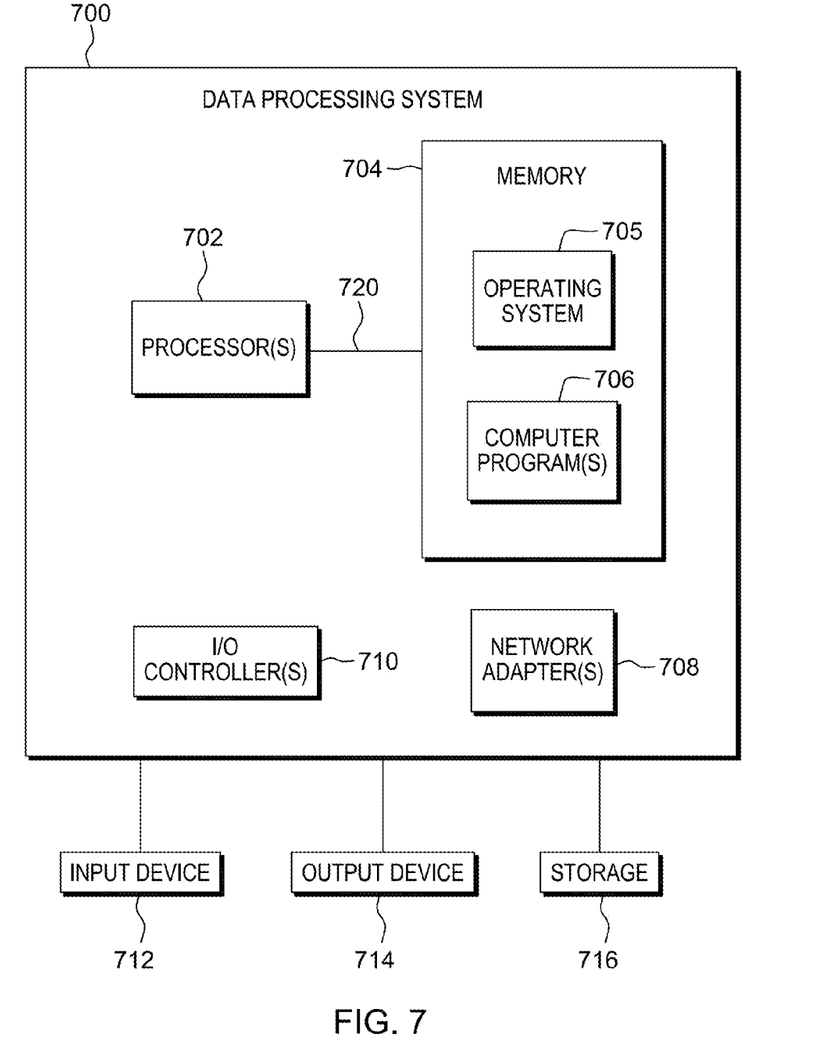
FIG. 7 depicts one example of a data processing system to incorporate and use aspects described herein.

FIG. 7 depicts one example of a data processing system to incorporate and use one or more aspects of the present invention. Data processing system 700 may be a data processing system of a measurement toolset (e.g. OCD toolset or XPS toolset), a host system in communication with one or more measurement toolsets, or a manufacturing execution system, Enterprise Resource Planning system, or Supervisory Control and Data Acquisition system, as examples.

Data processing system 700 is suitable for storing and/or executing program code, such as program code for performing processes described above, and includes at least one processor 702 coupled directly or indirectly to memory 704 through, a bus 720. In operation, processor(s) 702 obtain from memory 704 one or more instructions for execution by the processor(s). Memory 704 may include local memory employed during actual execution of the program code, bulk storage, and cache memories which provide temporary storage of at least some program code in order to reduce the number of times code must be retrieved from bulk storage during program code execution. A non-limiting list of examples of memory 704 includes a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Memory 704 includes an operating system 705 and one or more computer programs 706, such as one or more programs for execution to perform aspects described herein. In one particular example, a program performs the process of FIG. 6, described above by obtaining measurement data, the measurement data being output from an OCD measurement technique and a separate measurement technique. Additionally or alternatively, the program may be part of a measurement toolset, such as an OCD toolset or XPS toolset, or part of an MES, ERP, or SCADA system.

Input/Output (I/O) devices 712, 714 (including but not limited to keyboards, displays, pointing devices, etc.) may be coupled to the system either directly or through I/O controllers 710.

Network adapters 708 may also be coupled to the system to enable the data processing system to become coupled to other data processing systems through intervening private or public networks. Modems, cable modem and Ethernet cards are just a few of the currently available types of network adapters 708. In one example, network adapters 708 facilitate obtaining data from remote sources to facilitate aspects of the present invention.

Data processing system 700 may be coupled to storage 716 (e.g., a non-volatile storage area, such as magnetic disk drives, optical disk drives, a tape drive, etc.), having one or more databases. Storage 716 may include an internal storage device or an attached or network accessible storage. Computer programs in storage 716 may be loaded into memory 704 and executed by a processor 702.

The data processing system 700 may include fewer components than illustrated, additional components not illustrated herein, or some combination of the components illustrated and additional components. Data processing system 700 may include any computing device, such as a mainframe, server, personal computer, workstation, laptop, handheld computer, telephony device, network appliance, virtualization device, storage controller, etc.

In addition, processes described above may be performed by multiple data processing systems 700, working as part of a clustered computing environment.

In some embodiments, aspects of the present invention may take the form of a computer program product embodied in one or more computer readable medium(s). The one or more computer readable medium(s) may have embodied thereon computer readable program code. Various computer readable medium(s) or combinations thereof may be utilized. For instance, the computer readable medium(s) may include a computer readable storage medium, examples of which include (but are not limited to) one or more electronic, magnetic, optical, or semiconductor systems, apparatuses, or devices, or any suitable combination of the foregoing. Example computer readable storage medium(s) include, for instance: an electrical connection having one or more wires, a portable computer diskette, a hard disk or mass-storage device, a random access memory (RAM), read-only memory (ROM), and/or erasable-programmable read-only memory such as EPROM or Flash memory, an optical fiber, a portable compact disc read-only memory (CD-ROM), an optical storage device, a magnetic storage device (including a tape device), or any suitable combination of the above. A computer readable storage medium is defined to include a tangible medium that can contain or store program code for use by or in connection with an instruction execution system, apparatus, or device, such as a processor. The program code stored in/on the computer readable medium therefore produces an article of manufacture (such as a "computer program product") including program code.

Figure 8:
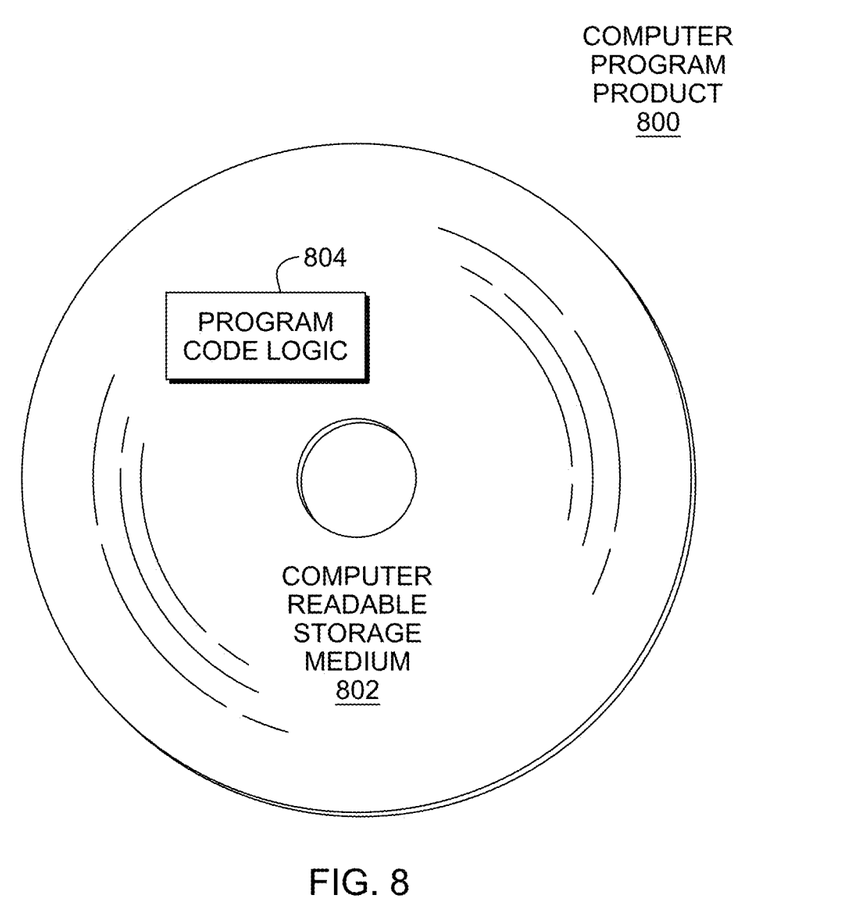
FIG. 8 depicts one embodiment of a computer program product incorporating aspects described herein.

Referring now to FIG. 8, in one example, a computer program product 800 includes, for instance, one or more computer readable media 802 to store computer readable program code means or logic 804 thereon to provide and facilitate one or more aspects of the present invention.

Program code contained or stored in/on a computer readable medium can be obtained and executed by a data processing system (computer, computer system, etc. including a component thereof) and/or other devices to cause the data processing system, component thereof, and/or other device to behave/function in a particular manner. The program code can be transmitted using any appropriate medium, including (but not limited to) wireless, wireline, optical fiber, and/or radio-frequency. Program code for carrying out operations to perform, achieve, or facilitate aspects of the present invention may be written in one or more programming languages. In some embodiments, the programming language(s) include object-oriented and/or procedural programming languages such as C, C++, C#, Java, etc. Program code may execute entirely on the user's computer, entirely remote from the user's computer, or a combination of partly on the user's computer and partly on a remote computer. In some embodiments, a user's computer and a remote computer are in communication via a network such as a local area network (LAN) or a wide area network (WAN), and/or via an external computer (for example, through the Internet using an Internet Service Provider).

In one example, program code includes one or more program instructions obtained for execution by one or more processors. Computer program instructions may be provided to one or more processors of, e.g., one or more data processing system, to produce a machine, such that the program instructions, when executed by the one or more processors, perform, achieve, or facilitate aspects of the present invention, such as actions or functions described in flowcharts and/or block diagrams described herein. Thus, each block, or combinations of blocks, of the flowchart illustrations and/or block diagrams depicted and described herein can be implemented, in some embodiments, by computer program instructions.

The flowcharts and block diagrams depicted and described with reference to the Figures illustrate the architecture, functionality, and operation of possible embodiments of systems, methods and/or computer program products according to aspects of the present invention. These flowchart illustrations and/or block diagrams could, therefore, be of methods, apparatuses (systems), and/or computer program products according to aspects of the present invention.

In some embodiments, as noted above, each block in a flowchart or block diagram may represent a module, segment, or portion of code, which includes one or more executable instructions for implementing the specified behaviors and/or logical functions of the block. Those having ordinary skill in the art will appreciate that behaviors/functions specified or performed by a block may occur in a different order than depicted and/or described, or may occur simultaneous to, or partially/wholly concurrent with, one or more other blocks. Two blocks shown in succession may, in fact, be executed substantially concurrently, or the blocks may sometimes be executed in the reverse order. Additionally, each block of the block diagrams and/or flowchart illustrations, and combinations of blocks in the block diagrams and/or flowchart illustrations, can be implemented wholly by special-purpose hardware-based systems, or in combination with computer instructions, that perform the behaviors/functions specified by a block or entire block diagram or flowchart.

Described herein, in some aspects, is a method that includes obtaining a measurement of thickness of a plurality of layers of a circuit structure, the thickness of the plurality of layers measured using an optical critical dimension (OCD) measurement technique, and the plurality of layers including a high-k layer and an interfacial layer. The method further includes separately obtaining a measurement of thickness of the high-k layer, the thickness of the high-k layer measured using a separate measurement technique from the OCD measurement technique and providing greater decoupling, as compared to the OCD measurement technique, of a signal for thickness of the high-k layer from a signal for thickness of the interfacial layer, and ascertaining, by a processor, a thickness of the interfacial layer using, in part, the separately obtained thickness measurement of the high-k layer. Also described herein, in some aspects, is a system that includes a memory and a processor in communications with the memory. The system can be configured to perform this method. Further described herein, in some aspects, is a computer program product that includes a computer readable storage medium readable by a processor and storing instructions for execution by the processor to perform this method.

The OCD measurement technique can include measuring a composite thickness, the composite thickness including thickness of the high-k layer and thickness of the interfacial layer, and the separate measurement technique can include detecting an emitted signal unique to the high-k layer and producing a corresponding spectra unique to the high-k layer. The separate measurement technique can include an electron-based measurement technique, such as x-ray photoelectron spectroscopy, x-ray fluorescence spectroscopy, and/or electron probe microanalysis.

The ascertaining of the thickness of the interfacial layer can include using the thickness measurement of the plurality of layers and using the separately obtained thickness measurement of the high-k layer in an OCD model of the OCD measurement technique to ascertain the thickness of the interfacial layer. Using the separately obtained thickness measurement of the high-k layer can include in this context using the separately obtained thickness measurement of the high-k layer as a seed value in the OCD model to facilitate decoupling the thickness of the high-k layer from the thickness of the interfacial layer in the OCD model. A variable for the thickness of the high-k layer in the OCD model can be fixed as the seed value, and/or the seed value can be used for weighing a variable for the thickness of the high-k layer in the OCD model.

The method can further include using the thickness measurement of the plurality of layers and the separately obtained thickness measurement of the high-k layer in the OCD model to ascertain other characteristics, such are one or more of critical dimension, height, and/or sidewall angle of the circuit structure.

The circuit structure can include a three-dimensional structure having at least one protruding surface, and the plurality of layers can be disposed at, or over a top of, the at least one protruding surface of the three-dimensional structure. In one particular example, the circuit structure includes a fin field-effect transistor (FinFET) or a nanostructure, and measurement of the thickness of the plurality of layers using the OCD measurement technique and measurement of the thickness of the high-k layer using the separate measurement technique are performed concurrently during fabrication of the FinFET or nanostructure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A method comprising:
   obtaining a measurement of thickness of a plurality of layers of a circuit structure, the thickness of the plurality of layers measured using an optical critical dimension (OCD) measurement technique, and the plurality of layers comprising a high-k layer and an interfacial layer;
   separately obtaining a measurement of thickness of the high-k layer, the thickness of the high-k layer measured using a separate measurement technique from the OCD measurement technique and providing greater decoupling, as compared to the OCD measurement technique, of a signal for thickness of the high-k layer from a signal for thickness of the interfacial layer; and
   ascertaining, by a hardware processor, a thickness of the interfacial layer using, in part, the separately obtained thickness measurement of the high-k layer,
   wherein the circuit structure comprises a fin field-effect transistor (FinFET) or a nanostructure, and wherein measurement of the thickness of the plurality of layers using the OCD measurement technique and measurement of the thickness of the high-k layer using the separate measurement technique are performed concurrently during fabrication of the FinFET or nanostructure.

2. The method of claim 1, wherein the OCD measurement technique comprises measuring a composite thickness, the composite thickness comprising thickness of the high-k layer and thickness of the interfacial layer, and wherein the separate measurement technique comprises detecting an emitted signal unique to the high-k layer and producing a corresponding spectra unique to the high-k layer.

3. The method of claim 2, wherein the separate measurement technique comprises an electron-based measurement technique.

4. The method of claim 3, wherein the electron-based measurement technique comprises at least one of: x-ray photoelectron spectroscopy, x-ray fluorescence spectroscopy, and electron probe microanalysis.

5. A method comprising:
   obtaining a measurement of thickness of a plurality of layers of a circuit structure, the thickness of the plurality of layers measured using an optical critical dimension (OCD) measurement technique, and the plurality of layers comprising a high-k layer and an interfacial layer;
   separately obtaining a measurement of thickness of the high-k layer, the thickness of the high-k layer measured using a separate measurement technique from the OCD measurement technique and providing greater decoupling, as compared to the OCD measurement technique, of a signal for thickness of the high-k layer from a signal for thickness of the interfacial layer; and
   ascertaining, by a hardware processor, a thickness of the interfacial layer using the separately obtained thickness measurement of the high-k layer and the thickness measurement of the plurality of layers in an OCD model of the OCD measurement technique to ascertain the thickness of the interfacial layer.

6. The method of claim 5, wherein using the separately obtained thickness measurement of the high-k layer comprises using the separately obtained thickness measurement of the high-k layer as a seed value in the OCD model to facilitate decoupling the thickness of the high-k layer from the thickness of the interfacial layer in the OCD model.

7. The method of claim 6, wherein a variable for the thickness of the high-k layer in the OCD model is fixed as the seed value.

8. The method of claim 6, wherein the seed value is used for weighing a variable for the thickness of the high-k layer in the OCD model.

9. The method of claim 5, further comprising using the thickness measurement of the plurality of layers and the separately obtained thickness measurement of the high-k layer in the OCD model to ascertain one or more of: (i) critical dimension, (ii) height, and (iii) sidewall angle of the circuit structure.

10. The method of claim 1, wherein the circuit structure comprises a three-dimensional structure having at least one protruding surface and wherein the plurality of layers are disposed at, or over a top of, the at least one protruding surface of the three-dimensional structure.

11. The method of claim 5, wherein the circuit structure comprises a fin field-effect transistor (FinFET) or a nanostructure, and wherein measurement of the thickness of the plurality of layers using the OCD measurement technique and measurement of the thickness of the high-k layer using the separate measurement technique are performed concurrently during fabrication of the FinFET or nanostructure.

12. A system comprising:
a memory; and
a hardware processor in communications with the memory, wherein the system is configured to perform a method comprising:
obtaining a measurement of thickness of a plurality of layers of a circuit structure, the thickness of the plurality of layers measured using an optical critical dimension (OCD) measurement technique, and the plurality of layers comprising a high-k layer and an interfacial layer;
separately obtaining a measurement of thickness of the high-k layer, the thickness of the high-k layer measured using a separate measurement technique from the OCD measurement technique and providing greater decoupling, as compared to the OCD measurement technique, of a signal for thickness of the high-k layer from a signal for thickness of the interfacial layer; and
ascertaining a thickness of the interfacial layer using, in part, the separately obtained thickness measurement of the high-k layer,
wherein the circuit structure comprises a fin field-effect transistor (FinFET) or a nanostructure, and wherein measurement of the thickness of the plurality of layers using the OCD measurement technique and measurement of the thickness of the high-k layer using the separate measurement technique are performed concurrently during fabrication of the FinFET or nanostructure.

13. The system of claim 12, wherein the OCD measurement technique comprises measuring a composite thickness, the composite thickness comprising thickness of the high-k layer and thickness of the interfacial layer, and wherein the separate measurement technique comprises detecting an emitted signal unique to the high-k layer and producing a corresponding spectra unique to the high-k layer.

14. The system of claim 13, wherein the separate measurement technique comprises an electron-based measurement technique.

15. A system comprising:
a memory; and
a hardware processor in communications with the memory, wherein the system is configured to perform a method comprising:
obtaining a measurement of thickness of a plurality of layers of a circuit structure, the thickness of the plurality of layers measured using an optical critical dimension (OCD) measurement technique, and the plurality of layers comprising a high-k layer and an interfacial layer;
separately obtaining a measurement of thickness of the high-k layer, the thickness of the high-k layer measured using a separate measurement technique from the OCD measurement technique and providing greater decoupling, as compared to the OCD measurement technique, of a signal for thickness of the high-k layer from a signal for thickness of the interfacial layer; and
ascertaining a thickness of the interfacial layer using the thickness measurement of the plurality of layers and using the separately obtained thickness measurement of the high-k layer in an OCD model of the OCD measurement technique to ascertain the thickness of the interfacial layer.

16. The system of claim 15, wherein the circuit structure comprises a fin field-effect transistor (FinFET) or a nanostructure, and wherein measurement of the thickness of the plurality of layers using the OCD measurement technique and measurement of the thickness of the high-k layer using the separate measurement technique are performed concurrently during fabrication of the FinFET or nanostructure.

17. A computer program product comprising:
a computer readable storage medium readable by a hardware processor and storing instructions for execution by the processor to perform a method comprising:
obtaining a measurement of thickness of a plurality of layers of a circuit structure, the thickness of the plurality of layers measured using an optical critical dimension (OCD) measurement technique, and the plurality of layers comprising a high-k layer and an interfacial layer;
separately obtaining a measurement of thickness of the high-k layer, the thickness of the high-k layer measured using a separate measurement technique from the OCD measurement technique and providing greater decoupling, as compared to the OCD measurement technique, of a signal for thickness of the high-k layer from a signal for thickness of the interfacial layer; and
ascertaining a thickness of the interfacial layer using the thickness measurement of the plurality of layers and using the separately obtained thickness measurement the high-k layer in an OCD model of the OCD measurement technique to ascertain the thickness of the interfacial layer.

18. The computer program product of claim 17, wherein the OCD measurement technique comprises measuring a composite thickness, the composite thickness comprising thickness of the high-k layer and thickness of the interfacial layer, and wherein the separate measurement technique comprises detecting an emitted signal unique to the high-k layer and producing a corresponding spectra unique to the high-k layer.

19. The computer program product of claim 18, wherein the separate measurement technique comprises an electron-based measurement technique.

20. The computer program product of claim 17, wherein using the separately obtained thickness measurement of the high-k layer in the OCD model comprises using the separately obtained thickness measurement of the high-k layer as a seed value in the OCD model to facilitate decoupling the thickness of the high-k layer from the thickness of the interfacial layer in the OCD model.

21. The system of claim 15, wherein using the separately obtained thickness measurement of the high-k layer in the OCD model comprises using the separately obtained thickness measurement of the high-k layer as a seed value in the OCD model to facilitate decoupling the thickness of the high-k layer from the thickness of the interfacial layer in the OCD model.

22. The computer program product of claim 17, wherein the circuit structure comprises a fin field-effect transistor (FinFET) or a nanostructure, and wherein measurement of the thickness of the plurality of layers using the OCD measurement technique and measurement of the thickness of the high-k layer using the separate measurement technique are performed concurrently during fabrication of the FinFET or nanostructure.

* * * * *